United States Patent [19]
Fristad et al.

[11] Patent Number: 5,106,541
[45] Date of Patent: Apr. 21, 1992

[54] MANGANESE COMPOUND CATALYZED OLIGOMERIZATION REACTIONS AND PRODUCTS THEREOF

[75] Inventors: William E. Fristad; Alan G. Olivero, both of Santa Rosa; Steven Young, Petaluma; Christopher S. Sykes; Brock M. Siegel, both of Santa Rosa, all of Calif.

[73] Assignee: Henkel Research Corporation, Santa Rosa, Calif.

[21] Appl. No.: 462,665

[22] Filed: Jan. 9, 1990

[51] Int. Cl.$^5$ .......................... C08H 3/00; C08H 5/00
[52] U.S. Cl. .................................. 554/213; 560/202; 562/590; 562/595; 562/887; 568/679; 568/680; 568/902
[58] Field of Search ................ 260/404, 407; 560/202; 562/590, 595, 887; 568/679, 680, 902

[56] References Cited

U.S. PATENT DOCUMENTS 3,308,140  3/1967  Roe et al. .............................. 260/404
3,641,120  2/1972  Broderick et al. .
3,927,077  12/1975  Finkbeimer et al. ................ 260/488

FOREIGN PATENT DOCUMENTS 0330203  8/1989  European Pat. Off. .
1927233  11/1969  Fed. Rep. of Germany .

Primary Examiner—José G. Dees
Assistant Examiner—Deborah D. Carr
Attorney, Agent, or Firm—Ernest G. Szoke; Wayne C. Jaeschke; Henry E. Millson, Jr.

[57] ABSTRACT

Oligomers and addition products obtained from the reaction of a saturated or olefinically unsaturated carboxylic acid, alcohol, ether, or ester with a substituted or unsubstituted acetic anhydride in the presence of a Mn compound, and processes for their preparation.

45 Claims, No Drawings

MANGANESE COMPOUND CATALYZED OLIGOMERIZATION REACTIONS AND PRODUCTS THEREOF

BACKGROUND OF THE INVENTION

1. Field of the Invention

This invention relates to processes for the preparation of addition products and oligomers, and to the addition products and oligomers produced thereby.

2. Statement of Related Art

The dimerization of alkanoic acids having an α-carbon atom to the corresponding succinic acids using a manganese salt of the alkanoic acid as an oxidative coupling agent in the presence of the anhydride of the alkanoic acid is known from related patents U.S. Pat. Nos. 3,845,116; 3,875,224; and U.S. Pat. No. 3,927,077. It is also known from published German application no. 19 27 233 that the oxidative coupling of vinylacetic acid to 1,5-hexadiene-1,6-dicarboxylic acid can be carried out in the presence of manganese dioxide. Published German Application No. 19 33 693 discloses the preparation of succinic acid from acetic acid in a 5% yield by oxidative coupling in the presence of manganese (III) acetate.

In "Free Radical Additions to Esters of Unsaturated Fatty Acids. Preparation of Dicarboxylic Acids and Other Polyfunctional Products", The Journal of the American Oil Chemists' Society, Vol. 42, pages 457-461, a process is described for peroxide intitiated free radical addition of acetic acid, acetic anhydride, or ethyl cyanoacetate to methyl undecylenate or methyl oleate in which the reaction products were mainly monoaddition products, with small quantities of dimers, trimers, and higher telomers. See also U.S. Pat. No. 3,308,140 which relates to, inter alia, the addition of acetic anhydride to the double bond of an unsaturated fatty acid ester to provide, after hydrolysis, a dicarboxylic acid having two more carbon atoms than the parent fatty acid.

In G.B. 1,409,659 a method is disclosed whereby unsaturated neo-carboxylic acids are prepared from the reaction of olefins with carboxylic acids in the presence of a reducible transition metal compound such as a manganese compound in the presence of a carboxylic acid anhydride, and wherein the resulting unsaturated neo-carboxylic acid can be further reaction with a carboxylic acid in the presence of a manganese compound and a carboxylic acid anhydride.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that saturated and unsaturated carboxylic acids, alcohols, ethers, and esters enter into addition reactions and can be oligomerized in high yields with relatively short reaction times when the addition and oligomerization reactions are carried out according to the following processes:

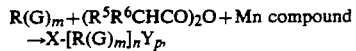

wherein $R(G)_m$ is a saturated or olefinically unsaturated carboxylic acid, carboxylic acid anhydride, alcohol, ether, or ester in which R is a saturated or unsaturated straight chain, branched, or carbocylic alkyl or alkenyl group containing from 4 to 60 carbon atoms, or an ether group of the formula $R^1OR^2$— in which $R^1$ is a $C_1$-$C_{59}$ straight chain or branched alkyl or alkenyl group, $R^2$ is a $C_1$-$C_{59}$ straight chain or branched alkyl or alkenyl group, and $R^1$ and $R^2$ together contain from 4 to 60 carbon atoms;

G is the carboxy group (—COOH) or an alkali or alkaline earth metal salt thereof, a $C_1$-$C_{20}$ alkoxycarbonyl group (—COOR$^3$, in which $R^3$ is a straight chain or branched alkyl or alkenyl group), the hydroxy group (—OH), a $C_1$-$C_{20}$ alkoxy or $C_2$-$C_{20}$ alkenyloxy group, or a $C_2$-$C_{20}$ alkanoyloxy group ($R^4$COO—, in which $R^4$ is a straight chain or branched $C_1$-$C_{19}$ alkyl or alkenyl group),

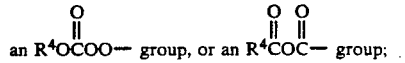

m is an integer of from 1 to 6;

$(R^5R^6CHCO)_2O$ is a carboxylic acid anhydride in which $R^5$ and $R^6$ are each independently —H or straight chain or branched $C_1$-$C_4$ alkyl;

the Mn compound is one or more of $MnO_2$, $Mn_2O_3$ or the Mn(III) salt of a carboxylic acid; and in the product $X$-$[R(G)_m]_n$-$Y_p$, X is hydrogen where R is a saturated group, and X is a $HO_2CR^5R^6C$— group or an $A^+$—$OOCR^5R^6C$— group where $A^+$ is an alkali or ½ an alkaline earth metal cation when R is an unsaturated group;

n is an integer of from 1 to 30 when unsaturated $R(G)_m$ reactants are employed, and from 2 to 30 where saturated $R(G)_m$ reactants are employed;

Y is one or more of —OH, —$CR^5R^6CO_2H$, —$CR^5R^6COO$—$A^+$, —$OCOCHR^5R^6$, or —$CR^5R^6C(O)OC(O)CHR^5R^6$, with the linkage between Y and R occurring at a random carbon atom of the R group when $R(G)_m$ is saturated and at a double bond carbon atom when $R(G)_m$ is unsaturated;

p is an integer of from 0 to 5; and

R, G, and m have the meanings given above, although it is to be understood that the R group in the product will not be identical to the R group present in unsaturated $R(G)_m$ reactants with respect to the number of double bonds present therein.

In the above compounds, the term "alkenyl" is understood to be an olefinically unsaturated alkyl group containing one or more double bonds in which the double bonds can be either conjugated or nonconjugated.

With respect to the reactant $R(G)_m$, this reactant is preferably a saturated or unsaturated carboxylic acid (alkanoic and alkenoic acids), or an alkali or alkaline earth metal salt thereof, or a simple ester thereof with a $C_1$-$C_4$ alkanol. The saturated and unsaturated carboxylic acids preferably include unsubstituted straight chain fatty acids having from 5 to 22, more preferably 8 to 18, carbon atoms. Examples thereof include the saturated fatty acids caproic, caprylic, capric, lauric, myristic, palmitic and stearic. Unsaturated fatty acids are for example palmitoleic, oleic, linolenic, linoleic, ricinoleic, undecylenic, elaidic, and arachidonic acids. While technical grade or even pure acids can be employed in the process of the invention, it is preferred to use fatty acid mixtures obtained from the hydrolysis of vegetable oils, e.g from coconut oil, i.e. a mixture consisting primarily of lauric acid, myristic acid, capric acid, palmitic acid, oleic acid, and stearic acid; from cottonseed oil, i.e. a mixture consisting primarily of linoleic acid, palmitic acid, oleic acid, and stearic acid; from peanut oil, i.e. a mixture consisting primarily of oleic acid, linoleic acid, and palmitic acid; from palm oil, i.e. a mixture consisting primarily of palmitic acid, oleic acid, lauric acid, and stearic acid; from rapeseed oil, i.e. a mixture consisting primarily of oleic acid, linoleic acid, and erucic acid; from safflower seed oil, i.e. a mixture consisting primarily of linoleic acid, oleic acid, stearic acid, and palmitic acid; from sesame seed oil, i.e. a mixture consisting primarily of oleic acid, linoleic acid, palmitic acid, and stearic acid; from soybean oil, i.e. a mixture consisting primarily of oleic acid, linoleic acid, linolenic acid, stearic acid, and palmitic acid; and from sunflower oil, i.e. a mixture consisting primarily of linoleic acid, oleic acid, palmitic acid, and stearic acid.

Saturated and unsaturated unsubstituted polycarboxylic acids or their salts can also be employed in the process of the invention, preferably those having from 5 to 20 carbon atoms, such as adipic acid, azelaic acid, suberic acid, and sebacic acid, and $C_{36}$ dimer (e.g. EMPOL® dimer acid, Emery Industries, Inc.) and $C_{54}$ trimer acids. Esters of the above mono- and polycarboxylic acids can also be employed in the process of the invention. The esters are preferably esters of $C_1$-$C_4$ alkanols, e.g. methyl, ethyl, propyl, isopropyl, butyl, and sec-butyl esters, with methyl most preferred. With respect to the dicarboxylic acids, both full and partial esters can be employed herein.

Mixtures of the above carboxylic acids and/or their salts, mixtures of the above esters, and mixtures of acids, their salts, and/or their esters can all be used in the practice of the invention. When the free acids are employed, the resulting polycarboxylic acid oligomer products can then optionally be esterified, using known esterification techniques. Also, if esters are used in the present process, the resulting oligomer which contains ester groups can be hydrolyzed to the corresponding free polycarboxylic acid oligomer, also by known techniques such as by acidic or basic hydrolysis, or the ester groups can be reduced, e.g. by hydrogenation, to produce the corresponding polyols.

In addition to the above unsubstituted straight chain carboxylic acids and their salts and esters, branched chain carboxylic acids and their salts and esters can also be employed.

When more than one G group is present in the compounds of the formula $R(G)_m$, i.e. when m is greater than 1, the G groups can be the same or different.

Where a G group is the $R^4COO-$ group, $R^4$ preferably contains from 1 to 5 carbon atoms.

With respect to the acid anhydride $(R^5R^6CHCO)_2O$, the corresponding free acid can also be employed at a ratio by weight of acid anhydride to acid of 50:1 to 1:1, preferably from 10:1 to 1:1, and more preferably at 3:1. The preferred acid anhydride for use herein is acetic anhydride, i.e. where $R^5$ and $R^6$ are both hydrogen. Where an acid anhydride is employed in which both $R^5$ and $R^6$ are branched, such as t-butyl, sec-butyl, or isopropyl groups, steric hindrance may interfere with the reaction, resulting in lower yields of product. Accordingly, anhydrides in which branched $R^5$ and $R^6$ groups are present are less desirable for use in the process of the invention.

When $R(G)_m$ represents a carboxylic acid anhydride, it is optional but preferred to use the acid $R^5R^6CHCOOH$, either alone or in admixture with the corresponding anhydride, in place of the $(R^5R^6CHCO)_2O$ reactant.

When the Mn compound is a Mn(III) salt of a carboxylic acid, the carboxylic acid is preferably the same as that used in the carboxylic acid anhydride $(R^5R^6CHCO)_2O$, although another carboxylic acid of the formula $R^5R^6CHCOOH$ can also be used to form the above Mn(III) salt.

The process is carried out at a reaction temperature in the range of 50° to 200° C., preferably at 100° to 150° C., and at a pressure ranging from atmospheric to 5 bar. It is preferred to carry out the reaction at atmospheric pressure under reflux conditions, e.g. using a reflux condenser. The above reaction temperature is maintained until a high yield of oligomeric product is obtained, usually from 2 to 24 hours, and generally from 3 to 5 hours, depending on the carboxylic acid, alcohol, ether, or ester starting material. Unsaturated acids, alcohols, ethers and esters tend to react more rapidly than saturated acids, ethers, alcohols, and esters. The manganese oxides and alkali metal salt are then filtered off from the oligomeric product, which is then isolated. One useful method for isolating the product is to first heat the reaction mixture, preferably under vacuum, to distill off free substituted or unsubstituted acetic acid and acetic anhydride. The reaction is preferably carried out in the absence of solvents.

The oligomeric products can optionally be treated with hydrogen peroxide, chlorine dioxide, sodium hypochlorite, or other known bleaching agent to produce a light-colored product.

The process of the invention produces oligomeric mixtures in high yields, e.g., of the order of 85 to 100% yields, and generally from 90% to 100%, based on the $R(G)_m$ starting material. This process is commercially feasible, producing not only high yields of oligomeric products, but also almost quantitative recovery of the manganese compounds, which is an important factor enabling the process to be economically practical.

In carrying out the reaction, it is optional but highly preferred to add to or have present in the reaction mixture an alkali metal or alkaline earth metal salt of the formula $R^5R^6CHCOO^-A^+$ where $R^5$ and $R^6$ have the meaning given above, and A is preferably an alkali metal cation, e.g. $Na^+$ or $K^+$, or an alkaline earth metal cation, e.g. $\frac{1}{2} Ca^{++}$ or $\frac{1}{2} Ba^{++}$. It is preferred but not essential that the $R^5$ and $R^6$ groups be identical to these in the carboxylic acid anhydride $(R^5R^6CHCO)_2O$ reactant. The presence of the above alkali metal or alkaline earth metal salt has been found to result in significantly higher yields and shorter reaction times.

The process of the invention can also be carried out by substituting a triglyceride, e.g. a naturally occurring vegetable or animal fat or oil, for the reactant $R(G)_m$. The resulting oligomeric product is however usually highly viscous, and must be saponified, e.g. using aqueous sodium hydroxide or potassium hydroxide, to produce a useful product. The free acid is obtained therefrom by acidification with a mineral acid such as hydrochloric or sulfuric acid.

The quantities of reactants and the Mn compound employed in the process of the invention, based on 1 mol of $R(G)_m$, are as follows:

$(R^5R^6CHCO)_2O$—from 1 to 120 mols, preferably 5 to 20 mols,

Mn compound—from 0.1 to 6 mols, preferably 0.5 to 4 mols, alkali metal or alkaline earth metal salt—from 0 to 2 mols, preferably 0.1 to 1 mols.

With respect to the acid $R^5R^6CHCO_2H$ when this acid is used as a component of the reaction mixture, the quantity thereof is employed within the ratio of anhydride to acid set forth above.

The product of the process of the invention, represented by mixtures of compounds of the formula $x\text{-}[R(G)_m]_n\text{-}Y_p$, can have an n value of from 1 to 30 for unsaturated $R(G)_m$ reactants, but is generally in the range of from 1 to 10, e.g. from 2 to 10. The value of n is somewhat dependent on the specific reactants and the reaction conditions for products obtained from olefinically unsaturated $R(G)_m$ reactants. For such unsaturated reactants, the value of n can be limited to 1, i.e. predominantly an addition product, by slow addition to the reaction mixture i.e. over a period of from 1 to 16 hours, of the unsaturated $R(G)_m$ reactant. To obtain reaction product in which n is greater than 1, i.e. the production of oligomers, all reaction components are added together. Where n is greater than 1, the R groups link together at the double bond sites to form the oligomers. However, if the reaction is forced, i.e. carried out under more extreme conditions, products can form in which R groups link to saturated carbon atoms.

With respect to the value of p in the product of the reaction, p can range from 0 to 5, e.g. 1 to 5, but usually is in the range of 0 to 1. The value of p is greater than 0 when the reaction conditions are selected near the upper ends of the temperature, time, and pressure ranges.

Where olefinically unsaturated reactants $R(G)_m$ are employed, the incorporation of the $HO_2CCR^5R^6$— group or an alkali or alkaline earth metal salt thereof (X) takes place at a double bond. Where R is polyunsaturated group, generally the addition of the above X group occurs at only one double bond. However, minor quantities of product in which two or more of the above X groups are present may be produced by the present process.

With respect to products resulting from saturated $R(G)_m$ reactants, as stated above, X is always hydrogen and n is an integer of from 2 to 30, generally from 2 to 10. For these products, the R groups link together randomly by what appears to be free radical coupling and accordingly the random structure of the resulting products are therefore structurally quite different from products resulting from unsaturated $R(G)_m$ reactants, which couple at a double bond carbon atom.

Where products are formed from a mixture of saturated and unsaturated $R(G)_m$ reactants, the resulting product will contain a mixture of the saturated and unsaturated $R(G)_m$ reactants, with the unsaturated reactants coupling at a double bond carbon atom and the saturated reactants coupling randomly at saturated carbon atoms by what appears to be a free radical mechanism.

The mixture of compounds of the formula $X\text{-}[R(G)_m]_n\text{-}Y_p$ that are obtained from the process of the invention can be isolated and used as such, or can be saponified using known acid or base saponification techniques to produce a saponified mixture of compounds of the above formula.

Mixtures of compounds of the above formula in which n is in the range of from 5 to 30 are novel, as are mixtures of such compounds in which n is in the range of from 3 to 30 and R is an alkyl or alkenyl group containing from 12 to 60 carbon atoms. In addition, mixtures of such compounds in which R is an ether group of the formula $R^1OR^2$— are also novel.

The acid, ester, alcohol, and ether addition and oligomer products of the present invention have a number of uses. They can be used as surfactants in cleaning compositions, e.g. in 0.1 to 5% by weight aqueous cleaning compositions for hard surfaces. They can also be used as foam inhibitors in detergent compositions for use in washing machines.

The invention will be illustrated but not limited by the following examples. In the examples GPC values are based on calibration using polystyrene as a calibration standard for examples 1–16 and standard methyl esters of monomer, dimer, and trimer acids as a calibration standard for examples 17–20, and are not intended to represent absolute molecular weights.

EXAMPLES

Example 1

Oligomerization of Undecylenic Acid

Two two-liter glass reactors equipped respectively with an overhead stirrer, a reflux condenser, a nitrogen inlet, and a thermocouple were each charged with acetic anhydride (600 ml), undecylenic acid (500 grams, 2.70 moles), acetic acid (200 ml), sodium acetate (111.2 grams, 1.35 moles), and manganese dioxide (119.7 grams, 1.35 moles). Each reactor was then heated to reflux (approximately 140° C.) and stirred at a temperature as to maintain reflux for five hours. The contents of each reactor were drained while still warm and the reactors rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (850 ml) and 50% KOH solution (ca. 950 ml) were added and the mixture stirred vigorously. The contents were then heated at a temperature of 100°–110° C. for fifteen hours at which time the reaction was acidified to a pH of 1 using 50% aqueous sulfuric acid (ca. 900 ml). The rate of acidification was such as to maintain a reaction temperature between 90° C. and 100° C. The aqueous layer was then syphoned out of the flask and replaced with hot water (ca. 1500 ml). The contents were stirred for approximately ten minutes and the aqueous layer again removed. This washing procedure was repeated a second time while maintaining a temperature of 90°–100° C. throughout the process. The organic product was poured into a two-liter round bottomed flask and the residual water removed in vacuo with heating to yield 973 grams of product as a dark paste. The conversion rate to oligomer was 96%, based on the undecylenic acid starting material.

| GPC: | $M_n$: 1310 | $M_w$: 2290 |
|---|---|---|
| Acid Value: | 332 mg KOH/g | |
| Sap. Value | 360 mg KOH/g | |
| Iodine Value: | 20 cg $I_2$/g | |
| Hydroxyl Value: | 24 mg KOH/g | |

| | |
|---|---|
| C: 69.2% | H: 10.0% |

Example 2

Oligomerization of Oleic Acid

Two two-liter glass reactors equipped respectively with an overhead stirrer, a reflux condenser, a nitrogen inlet, and a thermocouple were each charged with acetic anhydride (819 ml), oleic acid (500 grams, 1.77 moles), acetic acid (273 ml), sodium acetate (72.6 grams, 0.87 moles), and manganese dioxide (231 grams, 2.65 moles). Each reaction was then heated to reflux (approximately 140° C.) and stirred at a temperature as to maintain reflux for eight hours. The contents of each reaction were drained while still warm and the reactors rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (850 ml) and 50% KOH solution (ca. 950 ml) were added and the mixture stirred vigorously. The contents were then heated at a temperature of 100°-115° C. for fifteen hours at which time the reaction was acidified to a pH of 1 using 50% aqueous sulfuric acid (ca. 900 ml). The rate of acidification was such as to maintain a reaction temperature between 90° C. and 100° C. The aqueous layer was then syphoned out of the flask and replaced with hot water ca. 1500 ml). The contents were stirred for approximately ten minutes and the aqueous layer again removed. This washing procedure was repeated a second time while maintaining a temperature of 90°-100° C. throughout the process. The organic product was poured into a two-liter round bottomed flask and the residual water removed in vacuo with heating to yield 1045 grams of product as a dark thick liquid. The conversion to oligomeric material was 93%.

| GPC: | $M_n$: 890 | $M_w$: 1290 |
|---|---|---|
| Acid Value | 237 mg KOH/g | |
| Sap. Value | 288 mg KOH/g | |
| Iodine Value: | 14 cg $I_2$/g | |
| Hydroxyl Value: | 50 mg KOH/g | |
| C: 71.0% | H: 10.7% | |

Example 3

Oligomerization of Linoleic Acid

A 250 ml Morton flask equipped with an overhead stirrer, a reflux condenser, a nitrogen inlet, and a thermocouple were charged with acetic anhydride (25 ml), linoleic acid (12.01 g. 42 mmoles), acetic acid (8 ml), sodium acetate (3.5 grams, 42 mmoles), and manganese dioxide (5.47 grams, 63 mmoles). The reaction was then heated to reflux (approximately 140° C.) and stirred at a temperature as to maintain reflux for twelve hours. The contents of the reaction were drained while still warm and the reactor rinsed three times with a mixture of acetic acid and acetic anhydride (1:1). The rinses and the main reactor contents were combined and the solution filtered hot through a celite packed coarse fritted glass funnel. The filtrate was allowed to cool and the filtration repeated to remove precipitated salts. The solution was transferred to a round bottomed flask and the solvent removed in vacuo with heating. The residue was poured into a small Morton flask equipped with an overhead stirrer and a reflux condenser. A KOH solution (1.4M, ca. 400 ml) was added and the mixture stirred vigorously. The contents were then heated at a temperature of 100°-110° C. for 10 minutes and then stirred at room temperature for approximately 12 hours. The reaction was acidified to a pH of 1 using 3M aqueous hydrochloric acid. The mixture was taken-up in ether and methylene chloride (ca. 1:1). The organic layer was separated, dried over magnesium sulfate, filtered, and the solvent removed in vacuo with heating to yield ca. 11 grams of product as a dark liquid. The reaction was shown to have proceeded to approximately 97% conversion based on unreacted monomeric fatty acids.

Example 4

Oligomerization of Lauric Acid

Two two-liter glass reactors equipped respectively with an overhead stirrer, a reflux condenser, a nitrogen inlet, and a thermocouple were each charged with acetic anhydride (1045 ml), lauric acid (350 grams, 1.75 moles), acetic acid (350 ml), sodium acetate (71.8 grams, 0.88 moles), and manganese dioxide (608 grams, 7.0 moles). Each reaction mixture was then heated to reflux (approximately 140° C.) and stirred at a temperature as to maintain reflux for eight hours. The contents of each reactor were drained while still warm and the reactors rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (800 ml) and 50% KOH solution (900 ml) were added and the mixture stirred vigorously. The contents were then heated at a temperature of 100° C. for seventeen hours at which time the reaction was acidified to a pH of 1 using 50% aqueous sulfuric acid (ca. 900 ml). The rate of acidification was such as to maintain a reaction temperature between 90° C. and 100° C. The aqueous layer was then syphoned out of the flask and replaced with hot water (ca. 1500 ml). The contents were stirred for approximately ten minutes and the aqueous layer again removed. This washing procedure was repeated a second time while maintaining a temperature of 90°-100° C. throughout the process. The oligomer product was poured into a two-liter round bottomed flask and the residual water removed in vacuo with heating to yield 657 grams of product (86% conversion) as a dark liquid.

| GPC: | $M_n$: 1072 | $M_w$: 2020 |
|---|---|---|
| Acid Value | 203 mg KOH/g | |
| Sap. Value | 301 mg KOH/g | |
| Iodine Value | 10 cg $I_2$/g | |
| Hydroxyl Value: | 84 mg KOH/g | |

| | |
|---|---|
| C: 69.3% | H: 10.1 |

Example 5

Oligomerization of Stearic Acid

Two two-liter glass reactors equipped respectively with an overhead stirrer, a reflux condenser, a nitrogen inlet, and a thermocouple were each charged with acetic anhydride (945 ml), stearic acid (500 grams, 1.76 moles), acetic acid (315 ml), sodium acetate (72.2 grams, 0.88 moles), and manganese dioxide (611 grams, 7.0 moles). Each reaction was then heated to reflux (approximately 140° C.) and stirred at a temperature as to maintain reflux for eight hours. The contents of each reaction were drained while still warm and the reactors rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (800 ml) and 50% KOH solution (900 ml) were added and the mixture stirred vigorously. The contents were then heated at a temperature of ca. 100° C. for eighteen hours at which time the reaction was acidified to a pH of 1 using 50% aqueous sulfuric acid (ca. 850 ml). The rate of acidification was such as to maintain a reaction temperature between 90° C. and 100° C. The aqueous layer was then syphoned out of the flask and replaced with 35 hot water ca. 1500 ml). The contents were stirred for approximately ten minutes and the aqueous layer again removed. This washing procedure was repeated a second time while maintaining a temperature of 90°-100° C. throughout the process. The organic product was poured into a two-liter round bottomed flask and the residual water removed in vacuo with heating to yield 938 grams (ca. 93% yield) of product as a dark liquid. The reaction was determined to have proceeded to 82% conversion based on unreacted stearic acid.

| GPC: | $M_n$: 2000 | $M_w$: 3600 |
|---|---|---|
| Acid Value: | 152 mg KOH/g | |
| Sap. Value: | 221 mg KOH/g | |
| Iodine Value: | 10 cg $I_2$/g | |
| Hydroxyl Value: | 80.5 mg KOH/g | |
| C: 71.1% | H: 10.8% | |

Example 6

Oligomerization of Tallow Acids

A two-liter glass reactor equipped with an overhead stirrer, a reflux condenser, a nitrogen inlet, and a thermocouple, was charged with acetic anhydride (982 ml), tallow acids (500 grams, 1.81 moles), acetic acid (327 ml), sodium acetate (74.2 grams, 0.88 moles), and manganese dioxide (630 grams, 7.3 moles). The reaction was then heated to reflux (approximately 140° C.) and stirred at a temperature as to maintain reflux for eight hours. The contents of the reactor were drained while still warm and the reactor rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (1200 ml) and 50% KOH solution (400 ml) were added and the mixture stirred vigorously. The contents were then heated at a temperature of ca. 100° C. for 1.5 hours at which time the reaction was cooled to 50 degrees C. The contents were then treated with 5% NaOCl (1500 ml). The solution was filtered through a sintered glass funnel and acidified using 6N aqueous hydrochloric acid (ca. 850 ml). The rate of acidification was such as to maintain a reaction temperature between 90° C. and 100° C. The aqueous layer was then syphoned out of the flask and replaced with hot water (ca. 1500 ml). The contents were stirred for approximately ten minutes and the aqueous layer again removed. This washing procedure was repeated a second time while maintaining a temperature of 90°-100° C. throughout the process. The organic product was poured into a two-liter round bottomed flask and the residual water removed in vacuo with heating to yield 381 grams (ca. 76% yield) of product as a liquid. The reaction was determined to have proceeded to ca. 91% conversion based on unreacted monomeric acids.

| | |
|---|---|
| Acid Value: | 191 mg KOH/g |
| Sap. Value: | 295 mg KOH/g |
| Iodine Value: | 6 cg $I_2$/g |
| Hydroxyl Value: | 50 mg KOH/g |

Example 7

Oligomerization of Soya Fatty Acids

A 250 ml Morton flask equipped with an overhead stirrer, a reflux condenser, a nitrogen inlet, and a thermocouple were charged with acetic anhydride (75 ml), soya fatty acids (48 g, 171 mmoles), acetic acid (25 ml), sodium acetate (14 grams, 169 mmoles), and manganese dioxide (23.68 grams, 272 mmoles). The reaction was then heated to reflux (approximately 140° C.) and stirred at a temperature as to maintain reflux for six hours. The contents of the reaction were drained while still warm and the flask rinsed three times with a mixture of acetic acid and acetic anhydride (1:1). The rinses and the main reactor contents were combined and the solution filtered hot through a celite packed coarse fritted glass funnel. The solution was transferred to a round bottomed flask and the solvent removed in vacuo with heating. The residue was poured into a small Morton flask equipped with an overhead stirrer and a reflux condenser. A KOH solution (1.4M, ca. 800 ml) were added and the mixture stirred vigorously. The contents were then heated at a temperature of 100°-110° C. for five hours and then stirred at room temperature for approximately 12 hours. The reaction was acidified to a pH of 1 using 3M aqueous hydrochloric acid. The mixture was taken-up in ether. The organic layer was separated, dried over magnesium sulfate, filtered, and the solvent removed in vacuo with heating to yield ca. 45 grams of product as a liquid. The reaction was shown to have proceeded to approximately 91% conversion base on unreacted monomeric fatty acids.

| GPC: | $M_n$: 810 | $M_w$: 1130 |
| --- | --- | --- |
| Iodine Value: | 16 cg $I_2$/g | |

Example 8

Oligomerization of Methyl Oleate

A two-liter glass reactor equipped with an overhead stirrer, a reflux condenser, a nitrogen inlet, and a thermocouple was charged with acetic anhydride (907 ml), methyl oleate (500 grams, 1.71 moles), acetic acid (302 ml), sodium acetate (70.5 grams, 0.86 moles), and manganese dioxide (223 grams, 2.57 moles). The reaction was then heated to reflux (approximately 140° C.) and stirred at a temperature as to maintain reflux for eight hours. The contents of the reactor were drained while still warm and the reactor rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (850 ml) and 50% KOH solution (ca 950 ml) were added and the mixture stirred vigorously. The contents were then heated at a temperature of 100°–115° C. for fifteen hours at which time the reaction was acidified to a pH of 1 using 50% aqueous sulfuric acid (ca 900 ml). The rate of acidification was such as to maintain a reaction temperature between 90° C. and 100° C. The aqueous layer was then syphoned out of the flask and replaced with hot water (ca. 1500 ml). The contents were stirred for approximately ten minutes and the aqueous layer again removed. This washing procedure was repeated a second time while maintaining a temperature of 90°–100° C. throughout the process. The organic product was poured into a two-liter round bottomed flask and the residual water removed in vacuo with heating to yield 258 grams of product as a paste. The conversion to oligomeric material was 94%.

| Acid Value: | 255 mg KOH/g |
| --- | --- |
| Sap. Value: | 296 mg KOH/g |
| Iodine Value: | 14 cg $I_2$/g |
| Hydroxyl Value: | 39 mg KOH/g |
| C: 70.8% | H: 10.7% |

Example 9

Oligomerization of Methyl Stearate

A two-liter glass reactor equipped with an overhead stirrer, a reflux condenser, a nitrogen inlet, and a thermocouple was charged with acetic anhydride (885 ml), methyl stearate (500 grams, 1.68 moles), acetic acid (295 ml), sodium acetate (68.9 grams, 0.84 moles), and manganese dioxide (584 grams, 6.72 moles). The reaction was then heated to reflux (approximately 140° C.) and stirred at a temperature as to maintain reflux for eight hours. The contents of reaction vessel were drained while still warm and the reactor rinsed three times with 200 ml of a mixture of acetic acid and acetic anhydride (1.1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (475 ml) and 50% KOH solution (ca. 400 ml) were added and the mixture stirred vigorously. The contents were then heated at a temperature of 100°–110° C. for seventeen hours at which time the reaction was acidified to a pH of 1 using 50% aqueous sulfuric acid (ca 400 ml). The rate of acidification was such as to maintain a reaction temperature between 90° C. and 100° C. The aqueous layer was then syphoned out of the flask and replaced with hot water (ca. 750 ml). The contents were stirred for approximately ten minutes and the aqueous layer again removed. This washing procedure was repeated a second time while maintaining a temperature of 90°–100° C. throughout the process. The organic product was poured into a round bottomed flask and the residual water removed in vacuo with heating to yield approximately 450 grams of product as a dark paste.

Example 10

Oligomerization of Sunflower Oil Methyl Ester

A 250 ml Morton flask equipped with an overhead stirrer, a reflux condenser, a nitrogen inlet, and a thermocouple was charged with acetic anhydride (75 ml), sunflower oil ethyl ester (50.1 g, 169 mmoles), acetic acid (25 ml), sodium acetate (6.97 grams, 84 mmoles), and manganese dioxide (21.99 grams, 253 mmoles). The reaction was then heated to reflux (approximately 140° C.) and stirred at a temperature as to maintain reflux for five hours. The contents of the reaction were drained while still warm and the flask rinsed three times with a mixture of acetic acid and acetic anhydride (1:1). The rinses and the main reactor contents were combined and the solution filtered hot through a celite packed, coarse fritted glass funnel. The solution was transferred to a round bottomed flask and the solvent removed in vacuo with heating. The residue was taken-up in ether (ca. 200 ml) and washed four times with water (200 ml). The organic layer was separated, dried over magnesium sulfate, filtered, and the solvent removed in vacuo with heating to yield 53.2 g of a crude product. The reaction was shown to have proceeded to approximately 95% conversion based on unreacted monomeric esters.

| GPC: | $M_n$: 790 | $M_w$: 1140 |
| --- | --- | --- |
| Acid Value: | 74.5 mg KOH/g | |

Example 11

Oligomerization of Sebacic Acid

A two-liter glass reactor equipped with an overhead stirrer, a reflux condenser, a nitrogen inlet, and a thermocouple was charged with acetic anhydride (742 ml), sebacic acid (250 grams, 1.24 moles), acetic acid (248 ml), sodium acetate (51 grams, 0.62 moles), and manganese dioxide (431 grams, 4.96 moles). The reaction was then heated to reflux (approximately 140° C.) and stirred at a temperature as to maintain reflux for six hours. The contents of the reaction vessel were drained while still warm and the reactor rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a five-liter Morton flask equipped with an overhead stirrer and a reflux condenser. Water (150 ml) 50% KOH solution (ca. 150 ml) were added and the mixture stirred vigorously. The contents were then heated at a temperature of 100°-110° C. for twenty two hours at which time the reaction was acidified to a pH of 1 using 50% aqueous sulfuric acid (ca. 100 ml). The rate of acidification was such as to maintain a reaction temperature between 90° C. and 100° C. The aqueous layer was then syphoned out of the flask and replaced with hot water (ca. 750 ml). The contents were stirred for approximately ten minutes and the aqueous layer again removed. Hydrogen peroxide (125 ml of 30%) was added and the reaction stirred for approximately five hours. The aqueous layer was removed and the washing procedure was repeated a second time while maintaining a temperature of 90°-100° C. throughout the process. The aqueous layers were back extracted with ether (ca. 200 ml) and chloroform (ca. 400 ml). These back extractions were then combined with the original organic product and the solvent removed in vacuo with heating to yield approximately 206 grams of product as a dark solid.

Example 12

Oligomerization of Oleyl Alcohol

A 250 ml Morton flask equipped with an overhead stirrer, a reflux condensor, a nitrogen inlet, and a thermometer was charged with acetic anhydride (89 ml), oleyl alcohol (50 grams, 0.18 mmoles) acetic acid (13 ml), sodium acetate (7.7 grams, 0.09 moles), and manganese dioxide (24 grams, 0.28 mmoles). The reaction was then heated to reflux (approximately 140° C.) and stirred at a temperature as to maintain reflux for six hours. The contents of reaction vessel were drained while still warm and the reactor rinsed three times with 10 ml acetic acid. The rinses and the main reactor contents were combined and the solution filtered hot through a fritted glass funnel. The reaction mixture was transferred to a round bottomed flask and the solvent removed in vacuo with heating. A KOH solution (ca. 300 ml, 1.4M) was added and the mixture stirred vigorously. The contents were then heated at a temperature of 100°-110° C. for sixteen hours at which time the reaction was acidified to a pH of 1 using 3N hydrochloric acid (ca. 150 ml). The organic layer was separated and dissolved in ether (ca. 50 ml). The ether solution was washed three times with water (100 ml) and dried over anhydrous sodium sulfate. The solution was filtered and the solvent removed in vacuo with heating to yield 49.8 grams of product as a dark liquid.

| Acid Value: | 79.3 mg KOH/g |
|---|---|
| Sap. Value: | 141.4 mg KOH/g |
| OH Value: | 180.4 mg KOH/g |
| GC: | 0.77% Oleyl alcohol (99% conversion) |

Example 13

Oligomerization of Stearyl Alcohol

A 250 ml Morton flask equipped with an overhead stirrer, a reflux condensor, a nitrogen inlet, and a thermometer was charged with acetic anhydride (89 ml), stearyl alcohol (50 gram, 0.19 moles) acetic acid (13 ml), sodium acetate (7.6 grams, 0.09 moles), and manganese dioxide (64 grams, 0.74 mmoles). The reaction was then heated to reflux (approximately 140° C.) and stirred at a temperature as to maintain reflux for seven hours. The contents of reaction vessel were drained while still warm and the reactor rinsed three times with 10 ml acetic acid. The rinses and the main reactor contents were combined and the solution filtered hot through a fritted glass funnel. The solution was transferred to a one-liter Morton flask and the solvent removed in vacuo with heating. A 25% solution potassium hydroxide (ca. 80 ml) was added and the mixture stirred vigorously. The contents were then heated at a temperature of 100°-110° C. for 18 hours at which time the reaction was acidified to a pH of 1 using 50% sulfuric acid. The organic layer was separated and washed three times with water (250 ml). The residual water was removed in vacuo with heating to yield approximately 48 grams of product as a dark solid.

| Acid Value: | 39.4 mg KOH/g |
|---|---|
| Sap. Value: | 79.8 mg KOH/g |
| OH Value: | 253 mg KOH/g |
| GC: | 71% conversion |

Example 14

Oligomerization of Sunflower Oil

A 250 ml Morton flask equipped with an overhead stirrer, a reflux condenser, a nitrogen inlet, and a thermometer was charged with acetic anhydride (75 ml), new sunflower oil (12 grams, ca. 13 mmoles), acetic acid (25 ml), sodium acetate (3.48 grams, 0.04 moles), and manganese dioxide (7.76 grams, 89 mmoles). The reaction was then heated to reflux (approximately 140° C.) and stirred at a temperature as to maintain reflux for four hours. The contents of the reaction vessel were drained while still warm and the reactor rinsed three times with 10 ml acetic acid. The rinse and reaction mixture were combined and transferred to a round bottomed flask. The solvent was removed in vacuo with heating. A KOH solution (ca. 300 ml, 1.4M) was added and the mixture stirred vigorously. The contents were then heated at a temperature of 100°-110° C. for two hours at which time the reaction was acidified to a pH of 1 using 3N hydrochloric acid (ca 150 ml). The organic layer was separated and dissolved in ether (ca. 50 ml). The ether solution was washed three times with water (100 ml) and dried over anhydrous magnesium sulfate. The solution was filtered and the solvent removed in vacuo with heating to yield 11.1 grams of product as a dark liquid.

| GPC: | $M_n$: 940 | $M_w$: 1810 |
|---|---|---|

Example 15

Oligomerization of Dimethyl Sebacate

A two-liter glass reactor equipped with an overhead stirrer, a reflux condenser, a nitrogen inlet, and a thermocouple was charged with acetic anhydride (900 ml), dimethyl sebacate (300 grams, 1.3 moles), acetic acid (100 ml), sodium acetate (53.3 grams, 0.65 moles), and manganese dioxide (453 grams, 5.2 moles). The reaction was then heated to reflux (approximately 140° C.) and stirred at a temperature as to maintain reflux for eight hours. The contents of reaction vessel were drained while still warm and the reactor rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a Morton flask equipped with an overhead stirrer and a reflux condenser. Water (375 ml) and 50% KOH solution (375 ml) were added and the mixture stirred vigorously. The contents were then heated at a temperature of 95° C. for twenty hours and then allowed to cool to room temperature. The reaction was acidified to a pH of 1 using 50% aqueous sulfuric acid (ca. 100 ml). The organic layer was separated and the solvent removed in vacuo. Ethyl acetate (200 ml) was added and the organic layer washed with water several times. The solvent was removed in vacuo with heating to yield approximately 151 grams of product.

| Acid Value: | 409 mg KOH/g |
|---|---|
| Sap. Value: | 539 mg KOH/g |
| GPC: | $M_n$: 1100 |
| GC: | 14.4% sebacic acid present |

Example 16

Oligomerization of Dimethyl Azelate

A two-liter glass reactor equipped with an overhead stirrer, a reflux condenser, a nitrogen inlet, and a thermocouple was charged with acetic anhydride (810 ml), dimethyl azelate (251 grams, 1.15 moles), acetic acid (90 ml), sodium acetate (47.2 grams, 0.58 moles), and manganese dioxide (400.8 grams, 4.6 moles). The reaction was then heated to reflux (approximately 140° C.) and stirred at a temperature as to maintain reflux for eight hours. The contents of the reaction vessel were drained while still warm and the reactor rinsed three times with 200 ml of a mixture of acetic acid and acetic anhydride (1:1). The rinses and the main reactor contents were combined and the solution filtered hot through a two-liter coarse fritted glass funnel. The filtrate was allowed to cool and the filtration repeated to remove precipitated salts. The solution was transferred to a round bottomed flask and the solvent removed in vacuo with heating. The residue was poured into a Morton flask equipped with an overhead stirrer and a reflux condenser. Water (800 ml) and 50% KOH solution (ca. 300 ml) were added and the mixture stirred vigorously. The contents were then heated at a temperature of 95° C. for twenty one hours and then allowed to cool to room temperature. The reaction was acidified to a pH of 1 using 50% aqueous hydrochloric acid (ca. 100 ml) and a small volume of ethyl acetate added. The organic layer was separated and the solvent removed in vacuo. The residue was placed in a Morton flask to which hydrogen peroxide (40 ml of 30%) and water (100 ml) were added. The reaction was stirred at 80° C. for approximately 2.5 hours at which time ethyl acetate (200 ml) was added. The organic layer was washed with water and the solvent removed in vacuo with heating to yield approximately 116 grams of product.

| Acid Value: | 515.9 mg KOH/g |
|---|---|
| Sap. Value: | 597.2 mg KOH/g |
| GPC: | $M_n$: 800 |
| Ash: | 0.2% |

Example 17

Oligomerization of Isostearic Acid

A mixture of isostearic acid (409.7 g, 1.3 mol), sodium acetate (53.3 g, 0.65 mol), manganese dioxide Type HPM (452.1 g, 5.2 mol), acetic anhydride (750 ml) and acetic acid (310 ml) were heated to reflux under nitrogen with an overhead stirrer. After 8 hours the mixture was allowed to cool, suction filtered to remove manganese dioxide and manganese salts, and the filtrate stripped on a rotary evaporator. The residue was taken-up in water (600 ml) and potassium hydroxide (350 ml, 50% solution) and refluxed gently for 4 hours. The solution was acidified to pH=2 with concentrated hydrochloric acid. The warm mixture was allowed to separate into two layers and the bottom aqueous layer discarded. The organic layer was washed with warm water (3×) and divided into two equal portions One was dried on the rotary evaporator and possessed the following analytical values:

| Acid Value: | 167 mg KOH/g | |
|---|---|---|
| Sap. Value: | 245 mg KOH/g | |
| OH Value: | 52 mg KOH/g | |
| Iodine Value: | 10 cg $I_2$/g | |
| GPC: | $M_n = 486$ | $M_w = 1035$ |
| GC: | 21% isostearic acid | |

The second portion was bleached by heating with water (400 ml) and 30% hydrogen peroxide solution (100 ml) for 2 hours at 90° C. The aqueous layer was separated and the organic phase washed with 5% brine solution (2× until peroxide-free). The organic phase was next stirred rapidly with 10% hydrochloric acid (200 ml), and dropwise a 5% solution of sodium chlorite (200 ml) was added. The mixture was stirred at 80° C. for 1.5 hours. The aqueous phase was separated and the organic phase washed with 5% brine (3×). A brown fluid poly(isostearic) acid was obtained.

| Acid Value: | 162 mg KOH/g |
|---|---|
| Sap. Value: | 282 mg KOH/g |
| OH Value: | 33 mg KOH/g |
| Iodine Value: | 0 cg $I_2$/g |

Example 18

Oligomerization of Fore-cut Fatty acids

A mixture of fore-cut fatty acids (186 g, 1.2 mol, Vorlauffettsaure V85 KR, $C_8$–$C_{10}$, Henkel, KGaA, Duesseldorf, West Germany), sodium acetate (49.12 g, 0.6 mol) manganese dioxide (417.2 g, 4.8 mol), acetic anhydride (800 ml), and acetic acid (160 ml) was treated as in Example 17 and divided to give an unbleached and a bleached product with the following data:

| Unbleached: | |
|---|---|
| Acid Value: | 260 mg KOH/g |
| Sap. Value: | 360 mg KOH/g |
| OH Value: | 70 mg KOH/g |
| Iodine Value: | 5 cg $I_2$/g |
| GPC: | $M_n = 481$, $M_w = 974$ |
| GC: | 6% decanoic acid - octanoic acid not measured |
| Bleached: | |
| Acid Value: | 247 mg KOH/g |
| Sap. Value: | 385 mg KOH/g |
| OH Value: | 38 mg KOH/g |
| Iodine Value: | 1 cg $I_2$/g |

Example 19

Oligomerization of 2-Ethylhexanoic Acid

A mixture of 2-ethylhexanoic acid (331.7 g, 2.3 mol), sodium acetate (94.3 g, 1.15 mol), manganese dioxide (799.9 g, 9.2 mol) acetic anhydride (1531 ml), and acetic acid (306 ml) was treated an in Example 17 and divided to give an unbleached and a bleached product with the following data:

| Unbleached: | |
|---|---|
| Acid Value: | 228 mg KOH/g |
| Sap. Value: | 416 mg KOH/g |
| OH Value: | 29 mg KOH/g |
| Iodine Value: | 6 cg $I_2$/g |
| GPC: | $M_n = 395$, $M_w = 735$ |
| Bleached: | |
| Acid Value: | 216 mg KOH/g |
| Sap. Value: | 430 mg KOH/g |
| OH Value: | 10 mg KOH/g |
| Iodine Value: | 0 cg $I_2$/g |

Example 20

Oligomerization of Sunflower Fatty Acids

A mixture of sunflower fatty acids (277 g, 1 mol, Edenor ™ Sb 05, Henkel), sodium acetate (82.1 g, 1 mol) manganese dioxide (86.94 g, 1 mol), acetic anhydride (540 ml) and acetic acid (180 ml) was treated as in Example 17. The crude stripped product was stirred with water (400 ml), heated to 80°–90° C., and acidified to pH=3 with concentrated hydrochloric acid. After 2 hours of refluxing, the layers were separated. The organic phase was washed with 5% brine (3×), divided, and bleached as in Example 17. The bleached and unbleached products gave the following analytical data:

| Unbleached: | |
|---|---|
| Acid Value: | 234 mg KOH/g |
| Sap. Value: | 346 mg KOH/g |
| OH Value: | 2 mg KOH/g |
| Iodine Value: | 42 cg $I_2$/g |
| GPC: | $M_n = 588$, $M_w = 950$ |
| GC: | 2% oleic, linoleic acid |
| Bleached: | |
| Acid Value: | 220 mg KOH/g |
| Sap. Value: | 359 mg KOH/g |
| OH Value: | 25 mg KOH/g |
| Iodine Value: | 26 cg $I_2$/g |

We claim:

1. A process for the preparation of a mixture of oligomers of the formula $$X\text{-}[R(G)_m]_n\text{-}Y_p$$

wherein

R is a saturated or unsaturated straight chain, branched or carbocyclic alkyl or alkenyl group containing from 4 to 60 carbon atoms, or an ether group of the formula $R^1OR^2$— in which $R^1$ is a $C_1$–$C_{59}$ straight chain or branched alkyl or alkenyl group, $R^2$ is a $C_1$–$C_{59}$ straight chain or branched alkyl or alkenyl group, and $R^1$ and $R^2$ together contain from 4 to 60 carbon atoms;

G is —COOH, —COO$^-$A$^+$ where A$^+$ is an alkali metal or ½ an alkaline earth metal cation, —COOR$^3$ in which R$^3$ is a $C_1$–$C_{20}$ straight chain or branched alkyl or alkenyl group, —OH, a $C_1$–$C_{20}$ alkoxy group, a $C_2$–$C_{20}$ alkenyloxy group, an —OOCR$^4$ group in which R$^4$ is a straight chain or branched $C_1$–$C_{19}$ alkyl or alkenyl group, an $$-\underset{\underset{O}{\|}}{O}CR^4 \text{ group, or a } -\underset{\underset{O}{\|}}{C}\underset{\underset{O}{\|}}{O}CR^4 \text{ group;}$$

m is an integer of from 1 to 6;

n is an integer of from 1 to 30;

X is hydrogen where R is a saturated group and a —CR$^5$R$^6$CO$_2$H group of a —CR$^5$R$^6$CO$_2$$^-$A$^+$ group where R is an unsaturated group in which R$^5$ and R$^6$ are each independently —H or straight chain or branched $C_1$–$C_4$ alkyl;

Y is one or more of —OH, —CR$^5$R$^6$CO$_2$H, —CR$^5$R$^6$COO$^-$A$^+$, —OCOCHR$^5$R$^6$, or —CR$^5$R$^6$C(O)OC(O)CHR$^5$R$^6$, with the linkage between Y and R occurring at a random carbon atom of the R group where R is saturated and at a double bond carbon atom where R is unsaturated; and P is an integer of from 0 to 5; comprising the steps of:

A. reacting either (i) a saturated or olefinically unsaturated carboxylic acid or an alkali or alkaline earth metal salt thereof, carboxylic acid anhydride, alcohol, ether, or ester of the formula $$R(G)_m$$

wherein R, G, and m have a meaning give above, or (ii) a naturally occurring triglyceride, with a compound of the formula $$(R^5R^6CHCO)_2O$$

wherein R$^5$ and R$^6$ have the meaning given above, in the presence of a Mn compound which is one or more of MnO$_2$, Mn$_2$O$_3$, and the Mn(III) salt of a carboxylic acid of the formula R$^5$R$^6$CHCOOH in which R$^5$ and R$^6$ have the meaning given above, and in the presence of an alkali or alkaline earth metal salt of the formula R$^5$R$^6$CHCOO$^-$A$^+$ in which R$^5$, R$^6$, and A$^+$ have the meanings given above, at a temperature in the range of from about 50° C. to about 200° C. to form a reaction mixture containing a mixture of oligomers of the formula X-[R(G$_m$)]$_n$-Y$_p$ or a mixture of reacted triglycerides; and B. isolating the mixture of oligomers of the formula X-[R(G$_m$)]$_n$-Y$_p$ from the reaction mixture or, where a mixture of reacted triglycerides is present, saponifying the reacted triglycerides and then acidifying the saponified product to obtain said mixture of oligomers.

2. The process of claim 1 wherein in step A the reaction temperature is in the range of from about 100° C. to about 150° C.

3. The process of claim 1 wherein the reaction is carried out at a pressure ranging from atmospheric to about 5 bar.

4. The process of claim 1 wherein the reaction in step A is carried out for from about 2 to about 24 hours.

5. The process of claim 1 wherein R(G)$_m$ is an alkanoic acid, an alkenoic acid, an alkali or alkaline earth metal salt of the foregoing or a C$_1$-C$_4$ alkyl ester of the foregoing.

6. The process of claim 5 wherein the alkanoic or alkenoic acid or an alkali or alkaline earth metal salt thereof contains from 5 to 22 carbon atoms.

7. The process of claim 6 wherein said acid contains from 8 to 18 carbon atoms.

8. The process of claim 1 wherein R(G)$_m$ is a fatty acid mixture obtained from the hydrolysis of a vegetable or animal oil or fat.

9. The process of claim 1 wherein (R$^5$R$^6$CHCO)$_2$O is acetic anhydride.

10. The process of claim 1 wherein the reaction in step A is carried out at atmospheric pressure under reflux conditions.

11. The process of claim 1 wherein from about 1 to about 120 mols of (R$^5$R$^6$CHCO)$_2$O and from about 0.1 to about 6 mols of Mn compound are present, based on one mol of R(G)$_m$.

12. The process of claim 11 wherein from about 5 to about 20 mols of (R$^5$R$^6$CHCO)$_2$O and from about 0.5 to about 4 mols of Mn compound are present, based on one mol of R(G)$_m$.

13. The process of claim 1 wherein from about 0.1 to about 2 mols of R$^5$R$^6$CHCOO$^-$A$^+$ are present per mol of R(G)$_m$.

14. The process of claim 13 wherein from about 0.1 to about 1 mol of R$^5$R$^6$CHCOO$^-$A$^+$ are present per mol of R(G)$_m$.

15. The process of claim 1 wherein p is 0 or 1.

16. The process of claim 1 wherein the isolated mixture of oligomers from the R(G)$_m$ reaction in step B is then saponified.

17. The process of claim 1 wherein in step A R(G)$_m$ is a carboxylic acid anhydride, and is reacted with a compound of the formula R$^5$R$^6$CHCOOH or a mixture of a compound of the formula R$^5$R$^6$CHCOOH and a compound of the formula (R$^5$R$^6$CHCO)$_2$O.

18. The mixture of oligomers produced by the process of claim 1.

19. The mixture of oligomers produced by the process of claim 11.

20. The mixture of oligomers produced by the process of claim 16.

21. A process for the preparation of a mixture of oligomers of the formula H-[R(G)$_m$]$_n$-Y$_p$ wherein
R is saturated straight chain, branched, or carbocyclic alkyl group containing from 4 to 60 carbon atoms, or an ether group of the formula R$^1$OR$^2$— in which R$^1$ is a C$_1$-C$_{59}$ straight chain or branched alkyl group, R$_2$ is a C$_1$-C$_{59}$ straight chain or branched alkyl group, and R$^1$ and R$^2$ together contain from 4 to 60 carbon atoms;
G is —COOH, —COO$^-$A$^+$ where A$^+$ is an alkali metal ½ an alkaline earth metal cation, —COOR$^3$ in which R$^3$ is a C$_1$-C$_{20}$ straight chain or branched alkyl group, —OH, a C$_1$-C$_{20}$ alkoxy group, a —OOCR$^4$ group in which R$^4$ is a straight chain or branched C$_1$-C$_{19}$ alkyl group,

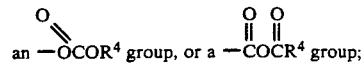
an —OCOR$^4$ group, or a —COCR$^4$ group;

m is an integer of from 1 to 6;
n is an integer of from 2 to 30;
Y is one or more of —OH, —CR$^5$R$^6$CO$_2$H, —CR$^5$R$^6$COO$^-$A$^+$, —OCOCHR$^5$R$^6$, or —CR$^5$R$^6$C(O)OC(O)CHR$^5$R$^6$, in which R$^5$ and R$^6$ are each independently —H or straight chain or branched C$_1$-C$_4$ alkyl, with the linkage between Y and R occurring at a random carbon atom of the R group; and
P is an integer of from 0 to 5; comprising the steps of:
A. reacting a saturated carboxylic acid or an alkali or alkaline earth metal salt thereof, carboxylic acid anhydride, alcohol, ether, or an ester of the formula R(G)$_m$ wherein R,G, and m have a meaning give above, with a compound of the formula (R$^5$R$^6$CHCO)$_2$O wherein R$^5$ and R$^6$ have the meaning give above, in the presence of an Mn compound which is one or more of MnO$_2$, Mn$_2$O$_3$, and the Mn(III) salt of a carboxylic acid of the formula R$^5$R$^6$CHCOOH in which R$^5$ and R$^6$ have the meaning give above, and in the presence of an alkali or alkaline earth metal salt of the formula R$^5$R$^6$CHCOO$^-$A$^+$ in which R$^5$, R$^6$ and A$^+$ have the meanings given above, at a temperature in the range of from about 50° C. to about 200° C. to form a reaction mixture containing a mixture of oligomers of the formula H-[R(G)$_m$]$_n$-Y$_p$; and B. isolating the mixture of oligomers of the formula H-[R(G)$_m$]$_n$-Y$_p$ from the reaction mixture.

22. The process of claim 21 wherein in Step A the reaction temperature is in the range of from about 100° C. to about 150° C.

23. The process of claim 21 wherein the reaction is carried out at a pressure ranging from atmospheric to about 5 bar.

24. The process of claim 21 wherein the reaction in step A is carried out for from about 2 to about 24 hours.

25. The process of claim 21 wherein R(G)$_m$ is an alkanoic acid, or an alkali or alkaline earth metal salt thereof, or a C$_1$-C$_4$ alkyl ester of the foregoing.

26. The process of claim 21 wherein from about 5 to about 20 mols of (R$^5$R$^6$CHCO)$_2$O and from about 0.5 to about 4 mols of Mn compound are present, based on one mol of R(G)$_m$.

27. The process of claim 21 wherein an acid of the formula $R^5R^6CHCO_2H$ is also present in step A in a ratio by weight of $(R^5R^6CHCO)_2O$ to $R^5R^6CHCO_2H$ of from about 50:1 to about 1:1.

28. The process of claim 27 wherein said ratio is from about 10:1 to about 1:1.

29. A process for the preparation of a mixture of oligomers of the formula $$X\text{-}[R(G)_m]_n\text{-}Y_p$$

wherein
R is an unsaturated straight chain, branched, or carbocyclic alkenyl group containing from 4 to 60 carbon atoms, or an ether group of the formula $R^1OR^2-$ in which $R^1$ is a $C_1$-$C_{59}$ straight chain or branched alkyl or alkenyl group, $R^2$ is a $C_1$-$C_{59}$ straight chain or branched alkyl or alkenyl group, and $R^1$ and $R^2$ together contain from 4 to 60 carbon atoms and at least one of $R^1$ and $R^2$ as an alkenyl group;

G is $-COOH$, $-COO^-A^+$ where $A^+$ is an alkali metal or ½ an alkaline earth metal cation, $-COOR^3$ in which $R^3$ is a $C_1$-$C_{20}$ straight chain or branched alkyl or alkenyl group, $-OH$, a $C_1$-$C_{20}$ alkoxy group, a $C_2$-$C_{20}$ alkenyloxy group, an $-OOCR^4$ group in which $R^4$ is a straight chain or branched $C_1$-$C_{19}$ alkyl or alkenyl group, $$\text{an } -\overset{O}{\underset{\|}{O}}CR^4 \text{ group, or an } -\overset{O}{\underset{\|}{C}}\overset{O}{\underset{\|}{O}}CR^4 \text{ group,}$$

m is an integer of from 1 to 6,
n is an integer of from 1 to 30;
X is a $-CR^5R^6CO_2H$ group or a $-CR^5R^6COO^-A^+$ group in which $R^5$ and $R^6$ are each independently $-H$ or straight chain or branched $C_1$-$C_4$ alkyl,
Y is one or more of $-OH$, $-CR^5R^6CO_2H$, $-CR^5R^6COO^-A^+$, $-OCOCHR^5R^6$, or $-CR^5R^6C(O)OC(O)CHR^5R^6$, with the linkage between Y and R occurring at a double bond carbon atom of the R group; and
p is an integer of from 0 to 5, comprising the steps of
A. reacting an olefinically unsaturated carboxylic acid or an alkali or alkaline earth metal salt thereof, carboxylic acid anhydride, alcohol, ether or ester of the formula $$R(G)_m$$

wherein R, G, and m have a meaning give above, with a compound of the formula $$(R^5R^6CHCO)_2O$$

wherein $R^5$ and $R^6$ have the meaning give above, in the presence of a Mn compound which is one or more of $MnO_2$, $Mn_2O_3$, and the Mn(III) salt of a carboxylic acid of the formula $R^5R^6CHCOOH$ in which $R^5$ and $R^6$ have the meaning give above, at a temperature in the range of from about 50° C. to about 200° C. to form a reaction mixture containing a mixture of oligomers of the formula $$X\text{-}[R(G)_m]_n\text{-}Y_p; \text{ and}$$

B. isolating the mixture of oligomers of the formula $X\text{-}[R(G)_m]_n\text{-}Y_p$ from the reaction mixture.

30. The process of claim 29 wherein G is $-COOR^3$ in which $R^3$ is a $C_1$-$C_{20}$ straight chain or branched alkyl or alkenyl group, $-OH$, a $C_1$-$C_{20}$ alkoxy group, a $C_2$-$C_{20}$ alkenyloxy group, an $-OOCR^4$ group in which $R^4$ is a straight chain or branched $C_1$-$C_{19}$ alkyl or alkenyl group, or an $$-\overset{O}{\underset{\|}{O}}COR^4 \text{ group.}$$

31. The process of claim 29 wherein $(R^5R^6CHCO)_2O$ is acetic anhydride.

32. The process of claim 29 wherein in step A in alkali metal or alkaline earth metal salt of the formula $R^5R^6CHCOO^-A^+$ where $R^5$ and $R^6$ are as defined in claim 1 and $A^+$ is an alkali metal cation or ½ an alkaline earth metal cation is also present in the reaction mixture.

33. A process for the preparation of a mixture of oligomers of the formula $X\text{-}[R(G)_m]_n\text{-}Y_p$
wherein
R is a saturated or unsaturated straight chain or branched alkyl or alkenyl group containing from 4 to 60 carbon atoms,
G is $-COOH$,
m is an integer of from 1 to 6,
n is an integer of from 1 to 30,
X is hydrogen where R is a saturated group and a $-CR^5R^6CO_2H$ group where R is an unsaturated group in which $R^5$ and $R^6$ are each independently $-H$ or straight chain or branched $C_1$-$C_4$ alkyl,
Y is one or more of $-OH$, $-CR^5R^6CO_2H$, $-O-COCHR^5R^6$, or $-CR^5R^6C(O)OC(O)CHR^5R^6$ with the linkage between Y and R occurring at a random carbon atom of the R group where R is saturated and at a double bond carbon atom where R is unsaturated;
p is an integer of from 0 to 5, comprising the steps of:
A. reacting a naturally occurring triglyceride with a compound of the formula $$(R^5R^6CHCO)_2O$$

wherein $R^5$ and $R^6$ have the meaning given above, in the presence of an Mn compound which is one or more of $MnO_2$, $Mn_2O_3$, and the Mn(III) salt of a carboxylic acid of the formula $R^5R^6CHCOOH$ in which $R^5$ and $R^6$ have the meaning given above, at a temperature in the range of from about 50° C. to about 200° C. to form a reaction mixture containing an oligomeric product,
B. saponifying the oligomeric product, and
C. acidifying the saponified product to obtain a mixture of oligomers of the formula $X\text{-}[R(G)_m]_n\text{-}Y_p$.

34. A process for the preparation of an addition product of the formula $$X\text{-}R(G)_m\text{-}Y_p$$

wherein
RF is a straight chain, branched, or carbocyclic alkenyl group containing from 4 to 60 carbon atoms, or an ether group of the formula $R^1OR^2$— in which $R^1$ is a $C_1$-$C_{59}$ straight chain or branched alkyl or alkenyl group, $R_2$ is a $C_1$-$C_{59}$ straight chain or branched alkyl or alkenyl group, and $R^1$ and $R^2$ together contain from 4 to 60 carbon atoms and at least one of $R^1$ and $R^2$ is an alkenyl group, G is —COOH, —COO$^-$A$^+$ where A$^+$ is an alkali metal or ½ an alkaline earth metal cation, —COOR$^3$ in which R$^3$ is a $C_1$-$C_{20}$ straight chain or branched alkyl or alkenyl group, —OH, a $C_1$-$C_{20}$ alkoxy group, a $C_2$-$C_{20}$ alkenyloxy group, an —OOCR$^4$ group in which R$^4$ is a straight chain or branched $C_1$-$C_{19}$ alkyl or alkenyl group,

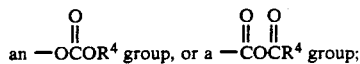
an —OCOR$^4$ group, or a —COCR$^4$ group;

m is an integer of from 1 to 6;

X is a —CR$^5$R$^6$CO$_2$H group or a —CR$^5$R$^6$COO$^-$A$^+$ group in which R$^5$ and R$^6$ are each independently —H or straight chain or branched $C_1$-$C_4$ alkyl, Y is one or more of —OH, —CR$^5$R$^6$CO$_2$H, —CR$^5$R$^6$COO$^-$A$^+$, —OCOCHR$^5$R$^6$, or —CR$^5$R$^6$C(O)OC(O)CHR$^5$R$^6$, with the linkage between Y and R occurring at a double bond carbon atom of the R group, and p is an integer of from 0 to 5, comprising the steps of A. reacting an olefinically unsaturated carboxylic acid, an alkali or alkaline earth metal salt of the foregoing, carboxylic acid anhydride, alcohol, ether or ester of the formula $R(G)_m$ wherein R, G, and m have a meaning given above, with a compound of the formula $(R^5R^6CHCO)_2O$ wherein R$^5$ and R$^6$ have the meaning given above in the presence of from about 0.1 to about 6 mols, per mol of R(G)$_m$, of an Mn compound which is one or more of MnO$_2$, Mn$_2$O$_3$, and the Mn(III) salt of a carboxylic acid of the formula R$^5$R$^6$CHCOOH in which R$^5$ and R$^6$ have the meaning given above, wherein the R(G)$_m$ reactant is added slowly over a period of from about 1 to about 16 hours and at a temperature in the range of from about 50° C. to about 200° C. to form a reaction mixture containing at least one addition product of the formula X-R(G)$_m$-Y$_p$, and B. isolating the at least one addition product of the formula X-R(G)$_m$-Y$_p$ from the reaction mixture.

35. The process of claim 34 wherein the reaction is carried out at a pressure ranging from atmospheric to about 5 bar.

36. The process of claim 34 wherein in step A an alkali metal or alkaline earth metal salt of the formula R$^5$R$^6$CHCOO$^-$A$^+$ where A$^+$ is an alkali metal or ½ an alkaline earth metal cation is also present in the reaction mixture.

37. A mixture of randomly coupled oligomers of the formula

H-[R(G)$_m$]$_n$-Y$_p$ wherein

R is a saturated straight chain, branched or carbocyclic alkyl group containing from 4 to 60 carbon atoms, or an ether group of the formula R$^1$OR$^2$— in which R$^1$ is a $C_1$-$C_{59}$ straight chain or branched alkyl group, R$^2$ is a $C_1$-$C_{59}$ straight chain or branched alkyl group, and R$^1$ and R$^2$ together contain from 4 to 60 carbon atoms, G is —COOH, —COO$^-$A$^+$ where A$^+$ is an alkali metal or ½ an alkaline earth metal cation, —COOR$^3$ in which R$^3$ is a $C_1$-$C_{20}$ straight chain or branched alkyl group, —OH, a $C_1$-$C_{20}$ alkoxy group, a —OOCR$^4$ group in which R$^4$ is a straight chain or branched $C_1$-$C_{19}$ alkyl group, an

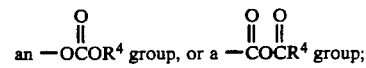
an —OCOR$^4$ group, or a —COCR$^4$ group;

m is an integer of from 1 to 6;

n is an integer of from 2 to 30;

Y is one or more of —OH, —CR$^5$R$^6$CO$_2$H, —CR$^5$R$^6$COO$^-$A$^+$, —OCOCHR$^5$R$^6$, or —CR$^5$R$^6$C(O)OC(O)CHR$^5$R$^6$, in which R$^5$ and R$^6$ are each independently —H or straight or branched chain $C_1$-$C_4$ alkyl, with the linkage between Y and R occurring at a random carbon atom of the R group, and p is an integer of from 1 to 5.

38. The mixture of oligomers of claim 37 wherein R is an alkyl group.

39. The mixture of oligomers of claim 38 wherein G is —COOH, —COO$^-$A$^+$, or COOR$^3$ in which R$^3$ contains from 1 to 4 carbon atoms.

40. The mixture of oligomers of claim 37 wherein p=1.

41. The mixture of oligomers of claim 37 wherein R is an alkyl group containing from 5 to 22 carbon atoms.

42. The mixture of oligomers of claim 41 wherein R contains from 8 to 18 carbon atoms.

43. The mixture of oligomers of claim 37 wherein the R(G)$_m$ moiety is obtained from a fatty acid mixture from the hydrolysis of a vegetable oil.

44. A mixture of oligomers of the formula:

X-[R(G)$_m$]$_n$-Y$_p$ wherein

R is a saturated or unsaturated straight chain, branched, or carbocyclic alkyl or alkenyl group containing from 4 to 60 atoms, or an ether group of the formula R$^1$OR$^2$— in which R$^1$ is a $C_1$-$C_{59}$ straight chain or branched alkyl or alkenyl group, R$^2$ is a $C_1$-$C_{59}$ straight chain or branched alkyl or alkenyl group, and R$^1$ and R$^2$ together contain from 4 to 60 carbon atoms;

G is —COOH, —COO$^-$A$^+$ where A$^+$ is an alkali metal or ½ an alkaline earth metal cation, —COOR$^3$ in which R$^3$ is a $C_1$-$C_{20}$ straight chain or branched alkyl or alkenyl group, —OH, a $C_1$-$C_{20}$ alkoxy group, a $C_2$-$C_{20}$ alkenyloxy group, an —OOCR$^4$ group in which R$^4$ is a straight chain or branched $C_1$-$C_{19}$ alkyl or alkenyl group, an 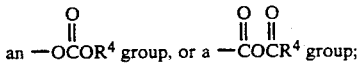

m is an integer of from 1 to 6;
n is an integer of from 5 to 30;
X is hydrogen where R is a saturated group and a —$CR^5R^6CO_2H$ group or a —$CR^5R^6COO^-A^+$ group where R is an unsaturated group in which $R^5$ and $R^6$ are each independently —H or straight chain or branched $C_1-C_4$ alkyl;
Y is one or more of —OH, —$CR^5R^6CO_2H$, —$CR^5R^6COO^-A^+$, —$OCOCHR^5R^6$, —$R^5R^6C(O)OC(O)CHR^5R^6$; and
p is an integer of from 0 to 5.

45. A mixture of oligomers of the formula:

$$X\text{-}[R(G)_m]_n\text{-}Y_p$$

wherein
R is a saturated or unsaturated straight chain, branched, or carbocyclic alkyl or alkenyl group containing from 12 to 60 carbon atoms;

G is —COOH, —$COO^-A^+$ where $A^+$ is an alkali metal or ½ an alkaline earth metal cation, —$COOR^3$ in which $R^3$ is a $C_1-C_{20}$ straight chain or branched alkyl or alkenyl group, —OH, a $C_1-C_{20}$ alkoxy group, a $C_2-C_{20}$ alkenyloxy group, an —$OOCR^4$ group in which $R^4$ is a straight chain or branched $C_1-C_{19}$ alkyl or alkenyl group, an

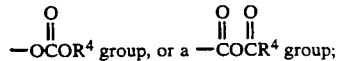

m is an integer of from 1 to 6;
n is an integer of from 3 to 30;
X is hydrogen where R is a saturated group and a —$CR^5R^6CO_2H$ group or a —$CR^5R^6COO^-A^+$ group where R is an unsaturated group in which $R^5$ and $R^6$ are each independently —H or straight chain or branched $C_1-C_4$ alkyl;
Y is one or more of —OH, —$CR^5R^6CO_2H$, —$CR^5R^6COO^-A^+$, —$OCOCHR^5R^6$, or —$CR^5R^6C(O)OC(O)CHR^5R^6$; and
p is an integer of from 0 to 5.

* * * * *